United States Patent [19]

Chen

[11] Patent Number: 5,569,203
[45] Date of Patent: Oct. 29, 1996

[54] SIMPLIFIED SAFETY SYRINGE WITH RETRACTABLE SELF-BIASED NEEDLE AND MINIMIZED PLUNGER

[76] Inventor: Long-Hsiung Chen, 5 F, No. 91-3, Chung Cheng Rd., Sec. 1, Taiwan, Taiwan

[21] Appl. No.: 493,936

[22] Filed: Jun. 23, 1995

[51] Int. Cl.⁶ ..................................................... A61M 5/00
[52] U.S. Cl. ............................................. 604/110; 604/195
[58] Field of Search .................................. 604/110, 195, 604/187, 263, 243, 192; 128/919

[56] References Cited

U.S. PATENT DOCUMENTS

| 5,378,240 | 1/1995 | Curie et al. | 604/110 |
| 5,395,346 | 3/1995 | Maggioni | 604/195 |

Primary Examiner—John D. Yasko
Attorney, Agent, or Firm—Bacon & Thomas

[57] ABSTRACT

A safety syringe for saving cost includes: a coupling member of arrowhead shape integrally formed with the thin-disk plunger, an annular ring embedded on the plunger to allow the plunger to be slibably held in the syringe for injection use, a syringe cylinder integrally formed with a sleeve portion on a front portion of syringe cylinder, an annular depression formed at the lower portion of said sleeve portion, a hollow needle which comprises a shank portion and a needle portion, said shank portion which connected with needle portion having a bias socket, said shank portion formed integrally a downward depression in it's rear portion from middle portion of the shank portion to somewhere beyond bias socket appropriate whereby upon retraction of the plunger and the coupled needle into the syringe, the needle will be inclined to prevent a further outward protruding of the retracted needle, and said shank portion could be held in the sleeve portion.

3 Claims, 4 Drawing Sheets

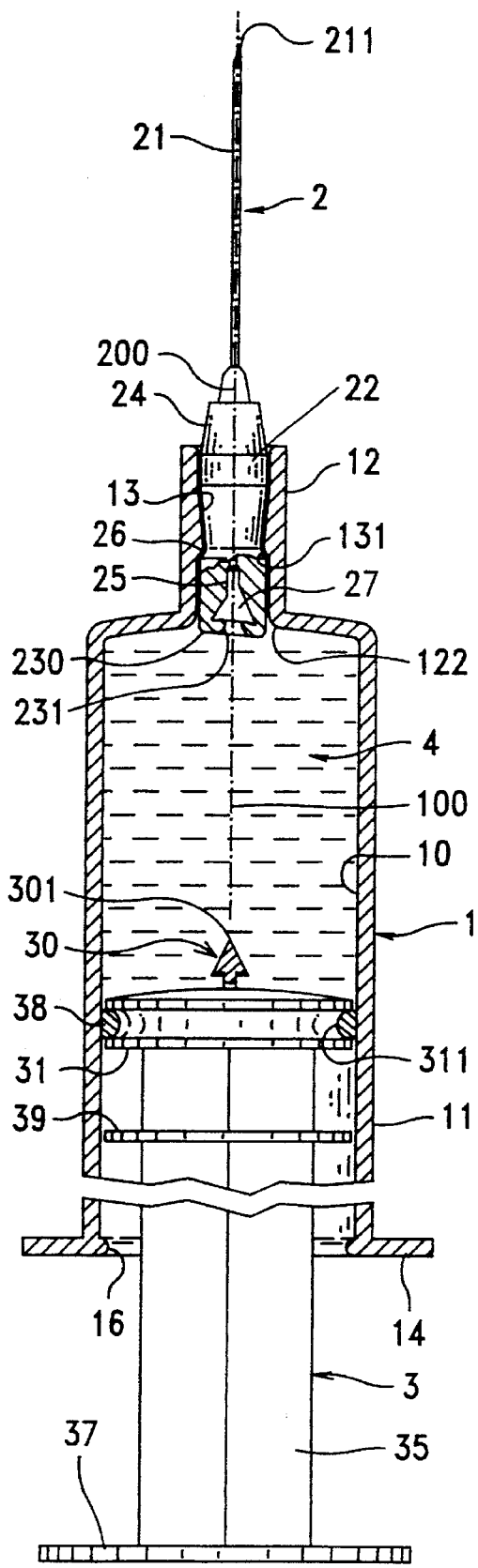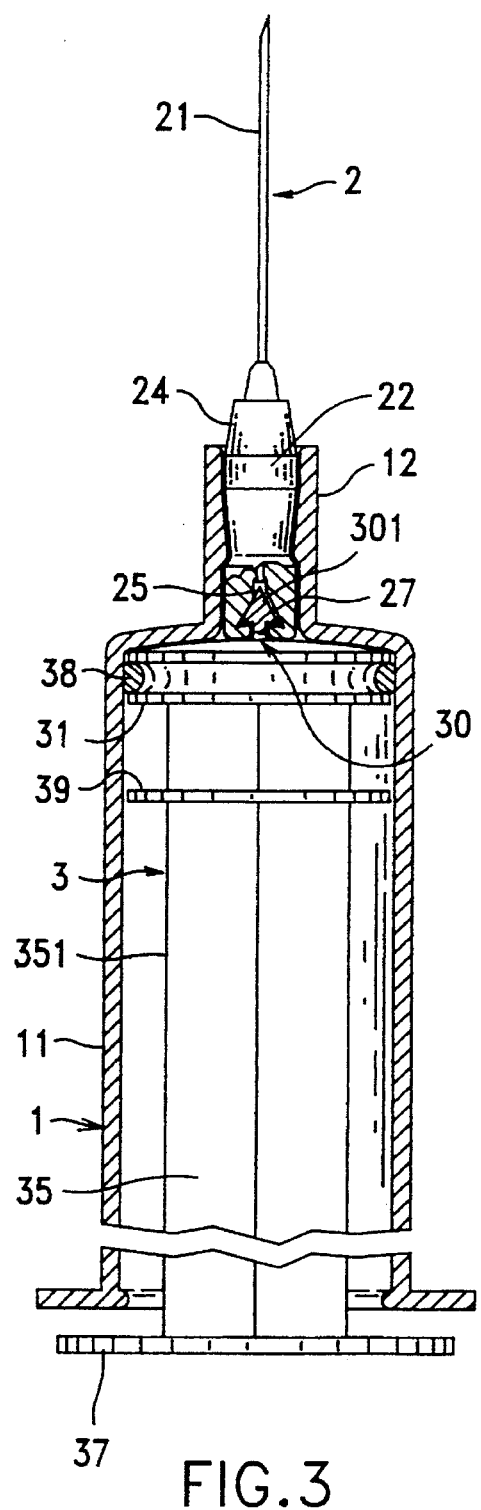

SIMPLIFIED SAFETY SYRINGE WITH RETRACTABLE SELF-BIASED NEEDLE AND MINIMIZED PLUNGER

BACKGROUND OF THE INVENTIONS

U.S. Pat. No. 5,402,327 entitled "Simplified Safety Syringe with Retractable Self-biased Needle" issued to the same inventor of this application diclosed a safety syringe including:a hollow needle normally held in a front portion of a syringe, a coupling member of arrowhead shape integrally formed with the thin-disk plunger, an annular ring embedded on the plunger to allow the plunger to be slibably held in the syringe for injection use, the coupling member formed on the plunger engageable with a biasing socket recessed in a rear needle portion of the hollow needle and with the biasing socket generally formed as a conical shape having a longitudinal conical axis inclined from a needle axis of the needle, wherby upon retraction of the plunger and the coupled needle into the syringe, the needle will be inclined to prevent a further outward protoruding of the retracted needle.

However, the needle portion 21 having an arcunte packing ving 26a circumferentialy disposed around the shank portion 22 to be engageably held in the ving groove 120a in the sleeve portion 12, Since the safety syringe is always made as disposable and will be disposed once being used for hygienic reason, such a big plunger, which is always made of resilient rubber materials, will waste money and will also increase a burden for waste disposal and treatment on a viewpoint of environmental protection.

SUMMARY OF THE INVENTION

The object of the present invention is to provide a safety syringe for saving cost and including: a coupling member of arrowhead shape integrally formed with the thin-disk plunger, an annular ring embedded on the plunger to allow the plunger to be slibably held in the syringe for injection use, a syringe cylinder integrally formed with a sleeve portion on a front portion of syringe cylinder, an annular depression formed at the lower portion of said sleeve portion, a hollow needle which comprising a shank portion and a needle portion, said shank portion which connected with needle portion having a bias socket, said shank portion formed integrally a downward depression in it's rear portin from middle portion of the shank portion to somewhere beyond bias socket appropriate whereby upon retraction of the plunger and the coupled needle into the syringe, the needle will be inclined to prevent a further outward protruding of the retracted needle, and said shank portion could be held in the sleeve portion.

BRIEF DESCRIPTION OF THE DRAWINGS

FIG. 2 is an illustration showing the present invention when served for injection use.

FIG. 3 shows coupling of the plunger with the needle when finishing a medical injection.

DETAILED DESCRIPTION

Figure 1:
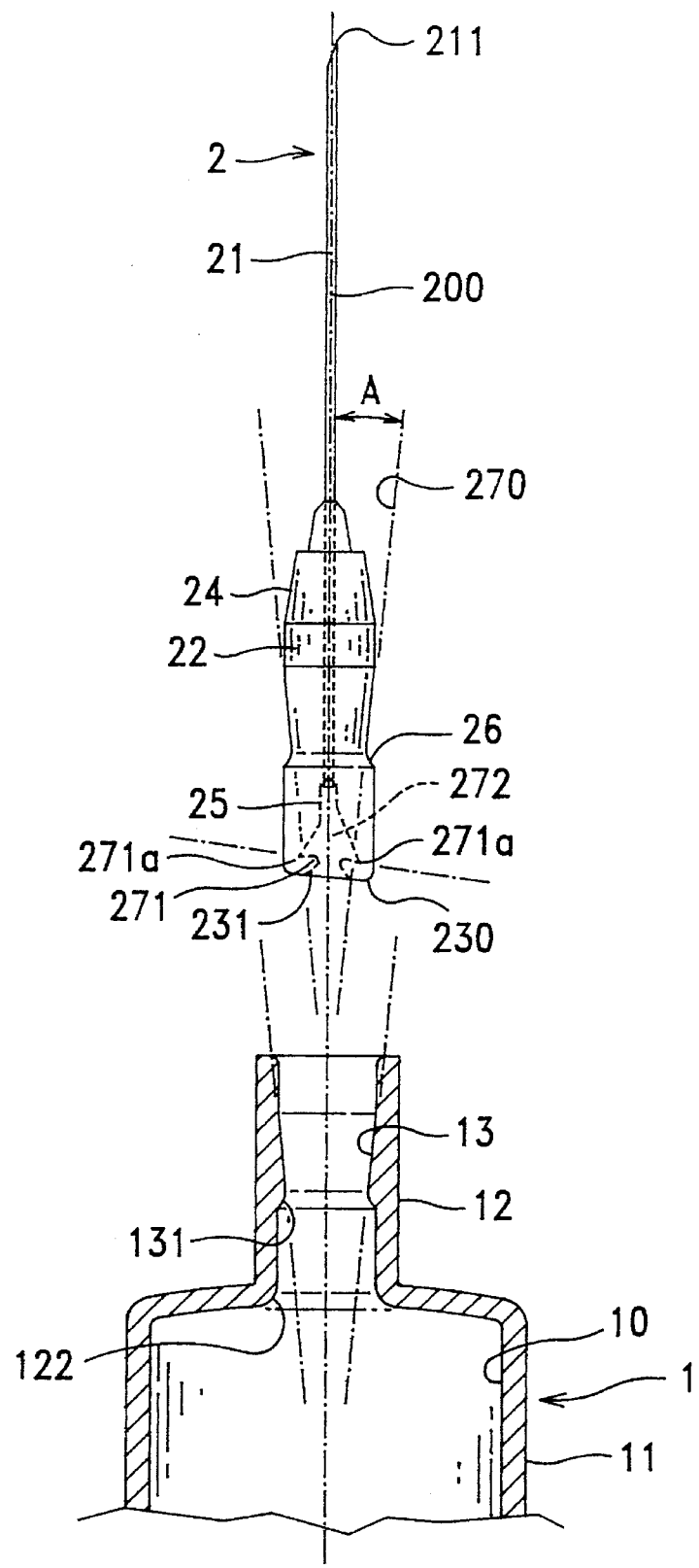
FIG. 1 is an illustration showing the syringe and the needle in accordance with the present invention.

As shown in the drawing figures, the present invention comprises: a syringe means 1, a needle device 2, and a plunger means 3.

The syringe means 1 includes: a syringe cylinder 11 having a hollow bore portion 10 defined in the syringe cylinder 11 for filling liquid medicine 4 in the cylinder 11 and a syringe axis 100 longitudinally defined in a central portion of the syringe cylinder 11, a sleeve portion 12 formed on a front portion of the syringe cylinder 11 contracted forwardly from the cylinder having a central opening 121 formed through the sleeve portion 12, and a diverging port 122 formed in a rear portion of the sleeve portion 12 adjacent to the syringe cylinder 11, an despression 120 longitudinaly and circumferentially recessed at the rear portion of the sleeve portion 12, a syringe handle 14 formed on a rear end portion of the cylinder 11, and an annular extension 16 annularly formed on a rear portion of the cylinder 11.

The needle device 2 includes: a needle portion 21 having a needle tip 211 formed at a front end of the needle portion 21, a shank portion 22 connected with the needle portion 21 having a downwand depresion at the lower inner of shank portion from middle of the shank portion to somewhere beyond bias socket appropriate, then formed an annular recess at the bottom of depression, whereby said shank portion could be held in the spring means. The shank portion 22 to be engageably held in the syringe means, a bifurcated slot 25 longitudinally formed in a rear portion of the shank portion 22 and recessed forwardly from a rear needle end portion 230, a biasing socket 27 generally conical shaped formed in a rear portion of the shank portion 22 and communicating with a guiding port 231 recessed forwardiy from the rear needle end portion 230, and a needle axis 200 longitudinally defined at a central portion of the needle device 2, with the shank protion 22 and the rear needle end portion 230 made of resilient plastic materials.

The needle axis 200 will be aligned with the syringe axis 100 when the needle device 2 is normally secured on a sleeve portion 12 of the syringe means 1 for injection purpose.

Each biasing socket 27 generally conical shaped includes: a conical bottom 271, a conical apex 272 tapered forwardly from the conical bottom 271, and a longitudinal conical axis 270 aligned with the conical apex 272 to be generally perpendicular to the conical bottom 271 and to be inclinedly deviated from the needle axis 200 of the needle device 2 to define an acute angle A between the needle axis 200 and the longitudinal conical axis 270 of the biasing socket 27. The conical bottom 271 includes a ratchet-tooth recess 271a circumferentially recessed in a rear portion of the shank portion 22 and tapered radially rearwardly from the conical bottom 271 of the biasing socket 27. The biasing socket 27 is snugly engageable with an arrowhead portion 301 of the plunger means 3 for obliquely biasing the needle device 2 when coupled to the plunger means 3 and retracted in the syringe cylinder 11 after finishing an injection.

The plunger means 3 includes: a thin-disk plunger 31a slibably held in the syringe cylinder 11 of the syringe means 3, a coupling member 30 integrally formed on a front portion of the plunger 31 having the arrowhead portion 301 formed on a from end of the coupling member 30 operatively insertable in the biasing socket 27 formed in the needle device 2, with the rear needle end portion 230 confined within the diverging port 122 formed in a rear portion of a sleeve portion 12 of the syringe means 1, a plunger rod 35 including three blades 351 protruding radially from a plunger axis 300 of the plunger means 3 integrally secured with a plunger handle 37 and protruding rearwardly from the plunger 31a and integrally connected to the plunger for pushing operation of the plunger 31a with the plunger 31a to be rearwardly retained on the an annular extension 16 formed in a rear portion of the syringe cylinder 11 for restriction a rear movement of the plunger 31a, and a plunger axis 300 longitudinally defined at a central portion of the syringe means 3 normally aligned with a needle axis 200 of the needle device 2, and aligned with the syringe axis 1 00 of the syringe means 1.

The coupling member 30 includes: te arrowhead portion 301 being conical shaped and engageable with the biasing socket 27 of conical shape of the needle device 2 having an apex of the arrowhead portion 301 aligned with the plunger axis 300, the needle axis 200 and the syringe axis 100 as shown in FIG. 1 ready for a normal medical injection, a neck ponger 31a.

The arrowhead portion 301 is formed with a ratchet tooth 301a circumferentially disposed around a rear end perimeter of the arrowhead portion 301 to be engaged with the ratchet-tooth recess 271a in the biasing socket 27 in the needle device 2 for ensuring a firm engagement of the coupling member 30 with the socket 27 of the needle device 2 for reliably coupling the needle device 2 with the plunger 31a when retracted into the syringe cylinder 11.

The plunger 31a is formed with an annular recess 311a along a periphery of the plunger 31a for embedding an annular packing ring 38 in the annular recess 31 1a for a smooth sealable sliding of the plunger 31a in the syringe cylinder 11. The annular packing ring 38 may have a cross sertion 302 connected between the arrowhead portion 301 and the pluction of circular shape, but not limited in this invention.

When using the present invention for injection use as shown in FIG. 2, the plunger 31a may be pushed for wardly to boost the medicine 4 in the cylinder 11 through the needle device 2 to a patient's body.

The arrowhead portion 301 of the coupling member 30 will then be forcibly inserted into the biasing socket 27 of the needle device 2 to squeeze, and expansively bifurcate the rear needle portion 230 of the needle device 20 to store a resilient potential energy of the bifucated rear needle portion, thereby operatively coupling the coupling member 30 with the needle device 2 as sown in FIG. 3.

Figure 4:
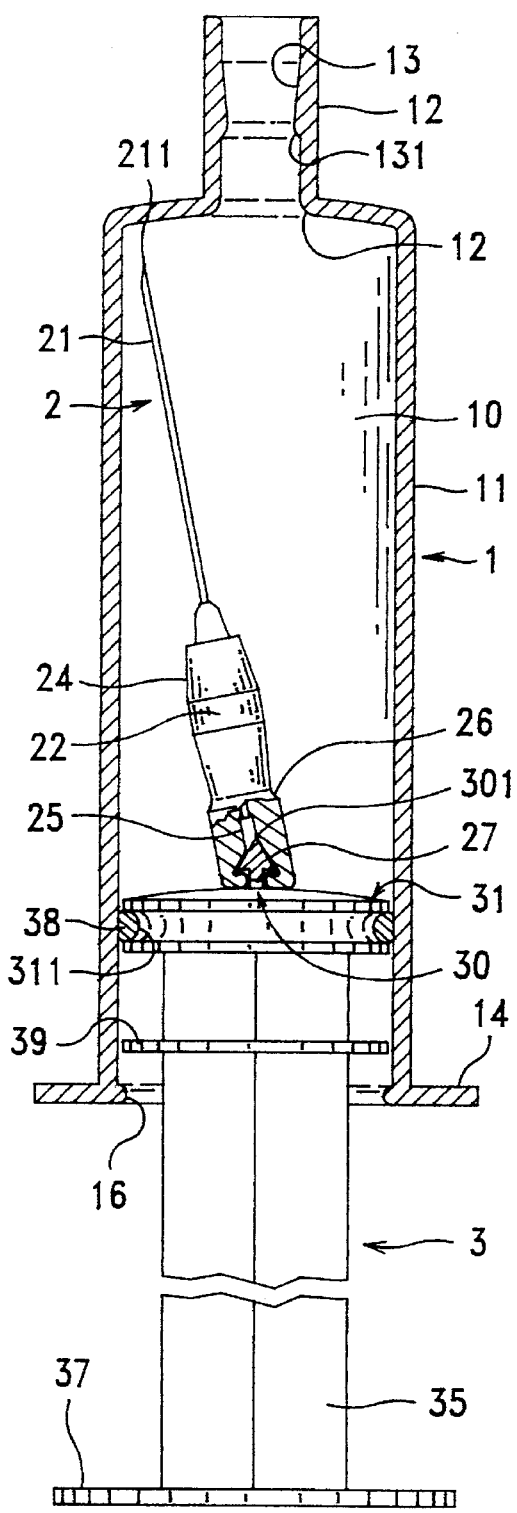
FIG. 4 shows retraction of needle into the syringe of the present invention.
Figure 5:
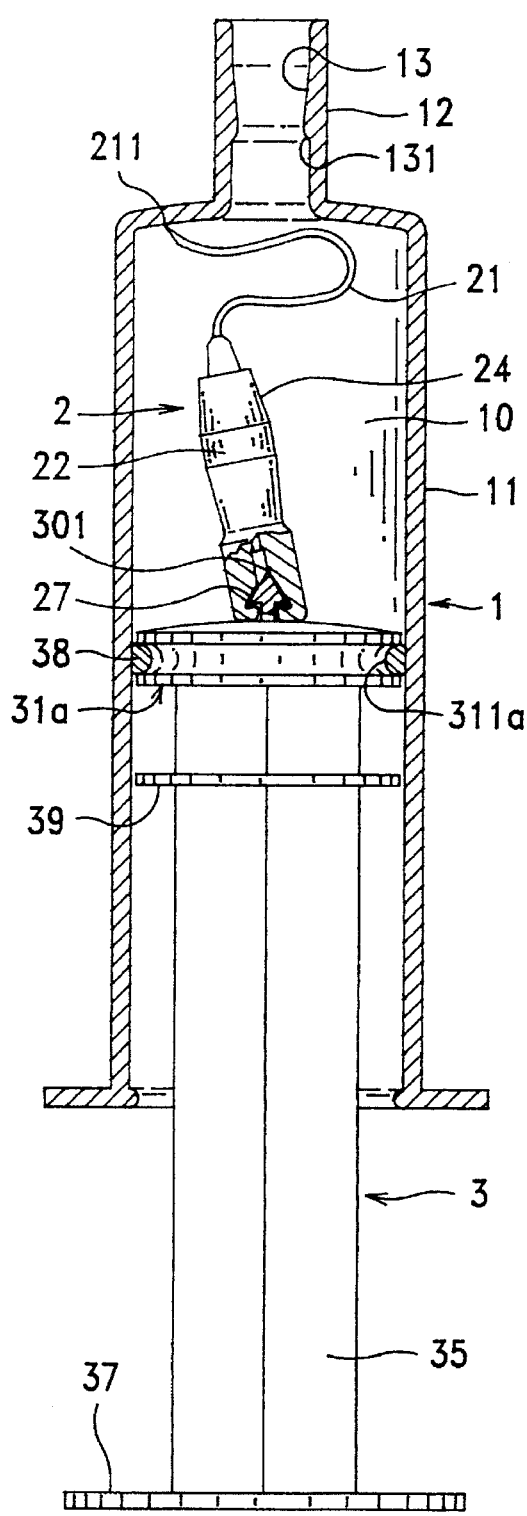
FIG. 5 shows a bent needle in the syringe in accordance with the present invention.

After retracting, the plunger 31a and the coupled needle device 2 into the bore portion 10 of the syringe cylinder 11 as shown in FIG. 4, the biasing socket 27 of the needle device 2 will be restored to be snugly engaged with the arrowhead portion 301 of the coupling member 30 of the plunger means 3 by releasing a resilient force accumulated on the rear needle portion 230 when forcibly coupling the arrowhead portion 301 with the biasing socket 27 as shown in FIG. 3, therby automatically obliquely biasing the needle device 2 coupled on the plunger 31a as shown in FIG. 4. After re-protruding the needle device 2 outwardly, the needle tip 211 will be retarded against a shoulder portion formed in a front portion of the cylinder 11, thereby bending the needle 2 and obstructing its outward protrusion and preventing its injury or contamination to the surroundings.

The present invention is superior to tim earlier invention, U.S. Pat. No. 5,405,327, also issued to the same inventor of this application since the the shank portion 22 of needle device 2 has been formed integvally and the plunger rod 35 of the earler invention has been minimized to merely include three blodes, thereby saving cost and being helpful for environmental protection.

The arrowhead portion 301, the neck portion 302, the plunger rod 35 and the handle 37 are all integrally formed shch as made by plastic molding process, and the annular ring 38 is then embedded in the recess 311a of the thin-disk plunger 31a.

Figure 6:
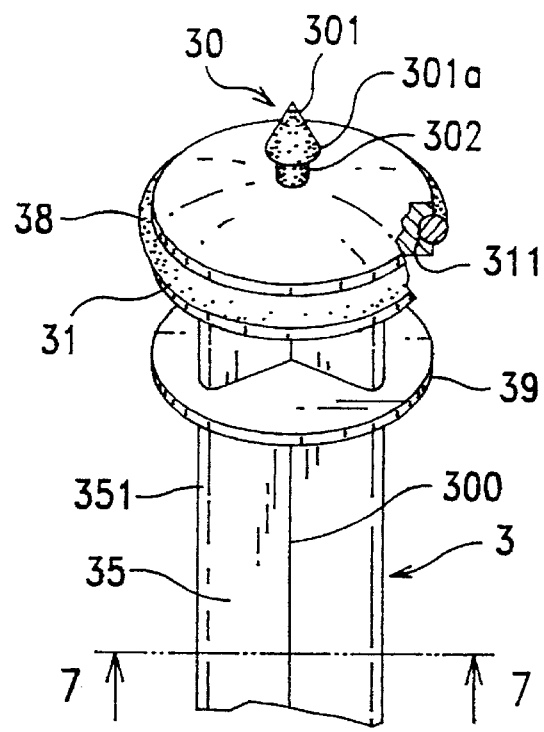
FIG. 6 is an illustration showing the plunger of the present invention is perspective view.
Figure 7:
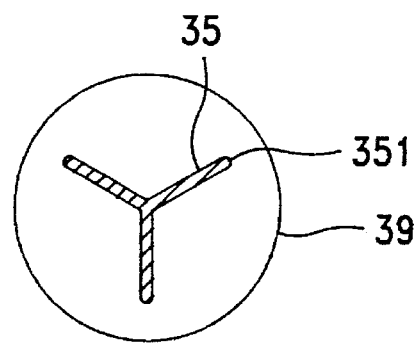
FIG. 7 is an illustration showing the plunger rod with three blades of the present inveniton in section view.

The plunger means 3 in its prefrred form shown in FIG. 6 provides additional thin disk 39 integrally formed with the plunger rod 35 at a front portion of said plunger rod 35, and been set and kept appropriate distance from said thin-disk plunger 31a, FIG. 7 is its section view.

I claim:

1. A safety syringe comprising a syringe means, a needle device and a plunger means, in which:

said syringe means includes a hollow cylinder for filling liquid medicine therein, and a reduced sleeve provided at a reduced shoulder on a front portion of said cylinder having a central opening formed a bottle-neck inside said sleeve, an outward flange and a inward stop ring provided to a rear edge of said cylinder thereon;

said needle device includes a hollow needle having a needle tip at a front portion, a resilient rubber shank fixedly held a rear portion of said needle having an annular recess between a cylindrical rear body and a streamline front body so as to be held in said sleeve of said syringe means by said bottle neck therein, said cylindrical rear body of said shank having a bias rear end surface and a bias conical space formed of an arrowhead socket with a ratchet-means gate at a center of said bias rear end surface led to a hollow center of said hollow needle through said arrowhead socket therefrom;

said plunger means is made of solid plastic comprising a plunger head having a annular ring groove and a plunger ring been received therein which slibably held in said cylinder of said syringe means to push liquid medicine for injection operation, an arrowhead coupling member forwardly disposed to a center of a front end of said plunger head having a ratchet-means neck at a root portion thereof which said arrowhead will be inserted into said bias arrowhead socket through said ratchet-means gate of said rear body of said shank and firmly engaged said needle device to said plunger means together as said ratchet-means neck of said arrowhead of said plunger head been caught by said ratchet-means gate of said shank while said plunger means been fully pushed forward during finished an injection operation, furthermore said bias arrowhead socket of resilient material been distorted to a right status from a bias status by said arrowhead of solid material forced thereinto, simultaneously an insilient strain been stored in the resilient material of said rear body of said shank which caused said needle tip to be biased to said sleeve of said syringe means inside said cylinder while said needle device been fully pulled back into said cylinder by a retracting of said plunger means after an injection operation and then said needle will be bent and destroyed and safely remain in said cylinder while said needle tip be blocked against said reducing shoulder of said cylinder during said plunger means been pushed again forwardly into said cylinder after a fully retracting of said plunger means; a thin disk provided to a plunger rod behind said plunger head to an appropriate distance for limiting a drawn back motion of said plunger means in contacting against to said stop ring of said cylinder thereof, a plunger rod formed of three blades protruding radially from a longitudinal center line of said plunger means disposed to a rear face of said plunger head and extended longitudinally out to said stop ring of said cylinder, and an end plate disposed to a rear end of said plunger rod for handling the pushing or pulling operation of said plunger means therefor.

2. A safety syringe as claimed in claim 1 wherein said plunger rod is formed of three blades radially from a longitudinal center line of said plunger means.

3. A safety syringe as claimed in claim 1 wherein said thin disk provided to said plunger rod has been set an appropriate distance from said plunger head to provide enough space for retracting whole said needle fully into said cylinder and to prevent said plunger means from being pulled off from said cylinder because of an abutment of said thin disk with said stop ring of said cylinder during a pulling back motion of said plunger means.

* * * * *